(12) United States Patent
Kwak et al.

(10) Patent No.: US 6,509,504 B1
(45) Date of Patent: Jan. 21, 2003

(54) METHOD FOR THE PRODUCTION OF SERINOL

(75) Inventors: Byong-Sung Kwak, Taejon (KR); Ki-Nam Chung, Taejon (KR); Choon-Gil Kim, Taejon (KR); Ki-Ho Koh, Taejon (KR)

(73) Assignee: SK Corporation, Seoul (KR)

( * ) Notice: Subject to any disclaimer, the term of this patent is extended or adjusted under 35 U.S.C. 154(b) by 0 days.

(21) Appl. No.: 09/936,062

(22) PCT Filed: Mar. 9, 2000

(86) PCT No.: PCT/KR00/00192

§ 371 (c)(1),
(2), (4) Date: Dec. 12, 2001

(87) PCT Pub. No.: WO00/53567

PCT Pub. Date: Sep. 14, 2000

(30) Foreign Application Priority Data

Mar. 9, 1999 (KR) ................................................ 99/7754

(51) Int. Cl.⁷ ............................................. C07C 215/10

(52) U.S. Cl. ........................................ 564/494; 564/495
(58) Field of Search .................................. 564/494, 495

(56) References Cited

U.S. PATENT DOCUMENTS 4,754,079 A * 6/1988 Bison et al. ................ 568/712

FOREIGN PATENT DOCUMENTS

EP 0 436 414 A1 * 7/1991 ......... C07C/213/02

* cited by examiner

Primary Examiner—Brian J. Davis
(74) Attorney, Agent, or Firm—Abelman, Frayne & Schwab

(57) ABSTRACT

Disclosed is a method for preparing serinol (2-amino-1,3-proanediol). From nitromethane, para-formaldehyde and sodium hydroxide, 1-nitro-1,3-propanediol sodium salt is prepared as a medical intermediate. In a fixed bed, this intermediate is allowed to undergo the continuous hydrogenation of 2-nitro-1,3-propanediol sodium salt and methanol as shown in reaction (1). In addition to being simple, the method is economically favorable and affords the high yield and high purity of serinol.

12 Claims, 1 Drawing Sheet

METHOD FOR THE PRODUCTION OF SERINOL

TECHNICAL FIELD

The present invention relates to a method for preparing serinol which is used as an intermediate in preparing a medical intermediate. More particularly, the present invention relates to a method for preparing serinol (2-amino-1,3-propanediol) of a high purity at high yield by reacting nitromethane with para-formaldehyde and then with sodium hydroxide as a sodium source to give 2-nitro-1,3-propanediol sodium salt and hydrogenating the sodium salt as in the following reaction in the presence of a metal or a metal-impregnated catalyst system.

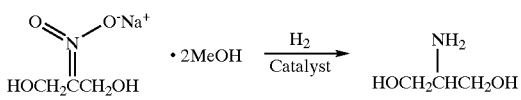

Serinol (2-amino-1,3-propanediol) is an intermediate for a medicine and in particular, is used as an intermediate useful for preparing Iopamidol, an X-ray contrast medium.

BACKGROUND ART

As described, in detail, in U.S. Pat. No. 4,754,079, 2-nitro-1,3-propanediol sodium salt, which is used as a raw material for serinol, can be prepared from nitromethane, paraformaldehyde, sodium methoxide and potassium hydroxide (KOH). The described preparation process in which KOH is used as a catalyst and sodium methoxide in a liquid phase (30% methanol solution) is utilized as a sodium source for 2-nitro-1,3-propanediol sodium salt, is disadvantageous in that the reaction is too complicated and the handling of the compounds is troublesome. In addition, the reaction between para-formaldehyyde and nitromethane must be carried out in a temperature range of 42 to 45° C. which is too narrow to control. Further, this process suffers from a problem of being economically unfavorable because sodium methoxide in a aligned phase is expensive compared with sodium hydroxide (NaOH) powder which is used in the present invention.

Another serinol preparation method can be referred to DE Pat. No. 2,742,981, in which 2-nitro-1,3-propanediol sodium salt is hydrogenated in a buffer acid to prepare serinol. In this method, hydrogen is absorbed in a stoichiometric amount, but the yield is merely 30 to 50% even under an ideal reaction condition. Another disadvantage of this method is that it is difficult to apply for industrial production because a Pd/C catalyst is hardly reusable.

According to U.S. Pat. No. 4,448,999, the production yield of serinol may be increased up to 74% by adopting a loop-type reactor equipped with effective cooling means and using methanol as a solvent. However, the batch reaction using a Pd/C catalyst, which is expensive and difficult to reuse, deters users from applying the method for industrial production. In addition, the catalyst must be removed vexatiously with a filter after reaction and the production yield is too low for industrial application.

U.S. Pat. No. 4,221,740 discloses the use of a Raney nickel instead of expensive Pd/C catalyst, asserting that the production yield of serinol can be increased to 64 to 87%. However, the Raney nickel catalyst is also not easy to reuse and requires a filter for its removal. In fact, the production yield is not sufficient.

Therefore, there remains a need for developing a preparation method for serinol which can be conducted even at relatively low temperatures, is economically favorable, and affords a high purity of serinol at a high production yield.

DISCLOSURE OF THE INVENTION

Accordingly, after intensive and thorough research the present inventors found that in the preparation of a 2-nitro-1,3-propanediol salt the use of sodium hydroxide (NaOH) powder as a sodium source unlike the conventional methods and the adoption of a fixed bed reactor system loaded with metals or a metal impregnated catalyst instead of using a conventional batch reactor can prevent the decrease in yield resulting from a reaction temperature rise and overcome the problems of heating para-formaldehyde for a complete dissolution. Based on these findings, the present invention, which is simple and economically favorable and can produce serinol with a purity at a high yield, became complete.

Therefore, it is an object of the present invention to provide a method for preparing serinol with a high purity at a high yield, which is simple and economically favorable.

In one embodiment of the present invention, there is provided a method for preparing serinol (2-amino-1,3-propanediol), comprising the steps of: reacting 1 equivalent of nitromethane with 1 to 10 equivalents of para-formaldehyde and then, adding 0.5 to 5 equivalents of sodium hydroxide to give 2-nitro-1,3-propanediol sodium salt; preparing a catalyst which comprises an inorganic support in which a catalytically effective metal component is impregnated at an amount of 1 to 20 wt %, said catalytically effective metal being selected from the group consisting of palladium (Pd), platinum (Pt), rhodium (Rh), iridium (Ir). ruthenium (Ru), osmium (Os) and mixtures thereof; and continuously hydrogenating the 2-nitro-1,3-propanediol sodium salt in a fixed bed reactor in which the catalyst is packed.

In one version of the embodiment, the present invention comprises of the reaction for preparing the 2-nitro-1,3-propanediol sodium salt at a temperature of 0 to 100° C. and the hydrogenation for preparing the 2-nitro-1,3-propanediol at a temperature of 0 to 150° C., a hydrogen pressure of 15 to 2,500 psig, and at a weight hourly space velocity (WHSV) of 0.1 to 10 $h^{-1}$ while feeding hydrogen/2-nitro-1,3-propanediol sodium salt at a molar ratio of 1 to 10 with a 1 to 50 wt % solution of 2-nitro-1,3-propanediol sodium salt in a solvent.

BEST MODES FOR CARRYING OUT THE INVENTION

In the present invention, nitromethane is first reacted with para-formaldehyde and the resulting compound is salted with sodium hydroxide under absence of catalysts to afford 2-nitro-1,3-propanediol sodium salt which is then allowed to undergo continuous hydrogenation when passing through a fixed bed reactor in which a catalyst comprising a metal or a metal-impregnated support is packed.

Different from conventional ones, the process for the preparation of 2-nitro-1,3-propanediol sodium salt in accordance with the present invention can be readily conducted even at relatively low temperatures. In addition, sodium hydroxide powder, which is used in the present invention, is relatively convenient to handle compared with the aqueous potassium hydroxide solution and sodium methoxide of liquid phase (30% methanol solution), which are conventionally used. In addition, the relatively cheap sodium hydroxide gives an economical advantage to the present invention.

For the preparation of the sodium salt, the amount of para-formaldehyde used preferably ranges from 1 to 10 equivalents per equivalent of nitromethane and more preferably from 1 to 5 equivalents. When the amount of para-formaldehyde is below 1 equivalent, the yield of the sodium salt is poor. On the other hand, when it is over 10 equivalents, side reactions occur.

As for sodium hydroxide, it is preferably used at an amount of 0.5 to 5 equivalents per equivalent of nitromethane and more preferably at an amount of 0.5 to 3 equivalents. Less than 0.5 equivalents of sodium hydroxide slows the reaction rate. On the other hand, greater than 5 equivalents of sodium hydroxide causes side reactions and an economical disadvantage.

The reaction temperature is set in the range of 0 to 100° C. and preferably 10 to 50° C. For instance, when the reaction is conducted at less than 0° C., the formation of the sodium salt is slow. On the other hand, when the reaction temperature exceeds 100° C., side reactions frequently occur to reduce the yield of the sodium salt yielding a colored mixture.

In accordance with the present invention, 2-nitro-1,3-propanediol sodium salt can be produced with a purity of 99.8% at a yield of 98%.

Subsequently, the 2-nitro-1,3-propanediol sodium salt is hydrogenated in the presence of a metal catalyst or a catalyst system comprising a metal-impregnated support, so as to produce serinol of a high purity at a high yield. This hydrogenation is accomplished in a continuous process using a fixed bed reactor. Therefore, the method of the present invention has an advantage over other processes using batch type processes, in production rate. In addition, the method of the present invention is economically favorable by virtue of the regeneration of the catalyst and not vexatious but simple because the catalyst needs not be removed by a filter system.

For the hydrogenation of 2-nitro-1,3-propanediol sodium salt into serinol, a suitable solvent should be used. This solvent is required to dissolve a solid salt of 2-nitro-1,3-propanediol sodium salt so sufficiently as to achieve the smooth feeding of the reactant into the reactor in addition to absorbing the reaction heat generated during the hydrogenation, an exothermic reaction, and not to react with the reactants, 2-nitro-1,3-propanediol sodium salt and hydrogen. Suitable for the hydrogenation of the present invention is one selected from the group consisting of methyl alcohol, ethyl alcohol, n-propyl alcohol, isopropyl alcohol, n-butyl alcohol, isopropyl alcohol, n-butyl alcohol, sec-butyl alcohol, tert-butyl alcohol, water and mixtures thereof with preference to a mixture of methyl alcohol and water. A mixture of 9:1 methyl alcohol:water is most preferable. In the solvent, 2-nitro-1,3-propanediol sodium salt is maintained at a concentration of 1 to 50 wt % and preferably 3 to 20 wt %. Further, the solvent can be heated to dissolve fully if required. If 2-nitro-1,3-propanediol sodium salt below 1 wt % is used, serinol is obtained at a poor yield. On the other hand, a content of greater than 50 wt % brings about a reduction in selectivity and conversion rate.

The hydrogenation of 2-nitro-1,3-propanediol sodium salt is carried out in the presence of a catalyst. This catalyst is either a metal itself or a metal impregnated in a support. The catalytically effective metal component is selected from the group consisting of nickel (Ni), palladium (Pd), platinum (Pt), rhodium (Rh), iridium (Ir), ruthenium (Ru), osmium (Os), and mixtures thereof with preference to palladium or ruthenium. As the support useful in the present invention, an inorganic oxide may be used. Examples of the inorganic oxide include alumina, silica, silica-alumina, zirconia, titania, zeolite and molecular sieves with most preference to alumina.

The support particles may be in a form of a sphere, a cylinder, a granule or any shape. However, they are preferably formed into spherical or cylindrical pellets for suitable mechanical properties.

When being impregnated in a support, the catalytically effective metal component is used at an amount of 1 to 20 wt % based on the weight of the total catalyst system and more preferably at an amount of 1 to 15 wt %. For instance, when the content of metal is below 1 wt %, the hydrogenation occurs slowly. On the other hand, when the content of metal is over 20 wt %, the expensive precious metal increases the production cost. When palladium or ruthenium is used as a catalytically effective metal component, the preferable content thereof is 5 to 20 wt % based on the total catalyst system.

Impregnation of the metal in the support may be carried out using an incipient wetness impregnation method, an excess water impregnation method, a spray method, or a physical mixing method.

After completion of the metal impregnation, the catalyst should be calcined for 2 hours or more in an air or an inert gas atmosphere. The calcination temperature ranges from 300 to 700° C. and preferably from 300 to 550° C. At a calcination temperature of less than 300° C., the metal precursor impregnated in the support is insufficiently decomposed. On the other hand, a calcination temperature of greater than 700° C. lowers the dispersion of the metal, resulting in a poor performance of the catalyst.

After being packed in a fixed bed reactor, the calcined catalyst is allowed to undergo the reduction with hydrogen prior to feeding the reactant into the reactor. This reduction condition should be maintained for at least 2 hours at 50 to 400° C. depending on the metals used.

A feature of the present invention resides in that a fixed bed reaction system is employed in which the catalyst is packed. The fixed bed reactor system guarantees higher space time yields, allows the catalyst to be reused, and makes the process simple. In the fixed bed reaction system, no limitations are imposed on the configuration of the reactor and the feeding type and flow direction of the reactant. In order to render the reactants to be brought into good contact with each other, however, there is preferably used a trickle-bed reactor in which the reactants hydrocarbons and hydrogen flow downwardly while being dispersed uniformly.

The preparation of serinol, resulting from the hydrogenation of 2-nitro-1,3-propanediol sodium salt, can be achieved under the condition of a hydrogen pressure of 15 to 2,500 psig, a reaction temperature of 0 to 150° C., and a weight hourly space velocity (WHSV) of 0.1 to 10 $h^{-1}$, preferably under the condition of a hydrogen pressure of 100 to 2,000 psig, a reaction temperature of 10 to 100° C., and a WHSV of 0.2 to 10 $h^{-1}$, and most preferably under the condition of a hydrogen pressure of 500 to 1,500 psig, a reaction temperature of 20 to 80° C., and a WHSV of 0.5 to 5 $h^{-1}$. A change in WHSV has a significant influence on the hydrogenation selectivity for serinol as shown in FIG. 1 in which the hydrogenation selectivities for serinol according to catalysts are plotted vs. WHSV. In addition, as will be elucidated later, the conversion and the selectivity in the hydrogenation of 2-nitro-1,3-propanediol sodium salt both increase with a particular amount of the catalyst used, but no more increase is obtained when the catalyst is used at an amount greater than the critical value, as shown in Table 2, below. Therefore, when the reaction condition is deviated from the above ranges, a decrease is found in the yield of serinol while an increase in the deactivation rate of the catalyst. Under such a deviated condition, advantage cannot be taken of the continuous process suggested by the present invention.

3.5 moles of hydrogen is sufficient to accomplish the complete conversion of 1 mole of 2-nitro-1,3-propanediol sodium salt by hydrogenation. The amount of the hydrogen fed is not limited if it is greater than 3.5 moles per mole of 2-nitro-1,3-propanediol, but the molar ratio of hydrogen to 2-nitro-1,3-propanediol is preferably determined in the range of 1–10 because of process economy. The hydrogen which is not reacted, but passes the reactor may be re-compressed and recycled to the reactor.

The reaction products effluent from the reactor are directed to a solvent-recovery unit in which at least a portion of the solvent used is separated from the other effluent components. This recovery unit may be one of any type, such as a distillation tower or a flash vaporizer. The products or concentrates effluent from a lower part of the solvent-recovery unit are transferred to a vacuum distillation apparatus.

Figure 1:
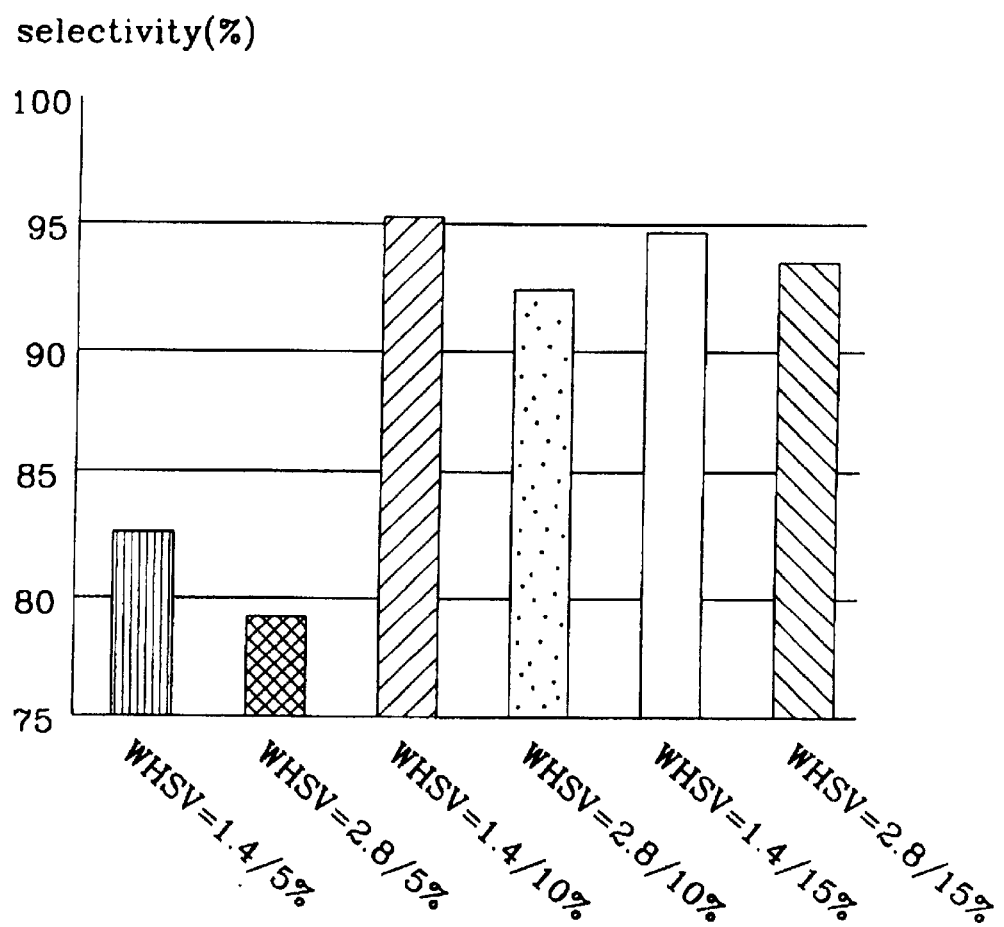
FIG. 1 is a graph in which the selectivity to serinol (2-amino-1,3-propanediol) is plotted vs. WHSV of hydrogen when 2-nitro-1,3-propanediol sodium salt is subjected to continuous hydrogenation in the presence of a catalyst ($Pd/Al_2O_3$ or $Ru/Al_2O_3$).

A better understanding of the present invention may be obtained in light of the following examples which are set forth to illustrate, but are not to be construed to limit the present invention.

Preparation Example 1

Preparation of 2-Nitro-1,3-Propanediol Sodium Salt

In a 1 L reactor equipped with a stirrer and a cooler, 60 g of nitromethane, 74.5 g of para-formaldehyde, 722 g of methanol, and 0.36 g of sodium hydroxide were charged, and the para-formaldehyde was dissolved at room temperature. Using the cooler, the internal temperature of the reactor was maintained at 35° C. or less, after which slow feeding of 43.9 g of sodium hydroxide afforded nitro-propanediol sodium salt as a white powder. In a nitrogen atmosphere, the powder was separated with a filter and dried in vacuum to obtain 2-nitro-1,3-propanediol sodium salt. Purity 99.8%, Yield 98%.

Preparation Example 2

Preparation of $Pd/Al_2O_3$

In a 100 cc flask was charged 50 cc of deionized water which was then added with 6.35 g of a palladium nitro compound ($Pd(NO_3)_2$, Aldrich). Into a vessel equipped with a variable speed motor set at 50 rpm was slowly added the Pd nitrate solution thus obtained to finely disperse the metal solution onto 100 g of ⅛" extrudate alumina (Norton). After completion of the feeding of the palladium nitro compound solution, the motor was rotated at the same speed for an additional 30 min. The palladium nitro compound-impregnated alumina thus obtained was calcined at 400° C. for 3 hours under an air atmosphere in a muffle furnace. An X-ray fluorescence analysis showed that the catalyst contained palladium of 10.0 wt %.

Preparation Example 3

Preparation of $Ru/Al_2O_3$

In a 100 cc flask was charged 40 cc of deionized water which was then added with 17.9 g of ruthenium chloride ($RuCl_3$, Aldrich). Into a vessel equipped with a variable speed motor set at 50 rpm was slowly added the ruthenium chloride solution thus obtained to finely disperse the metal solution onto 100 g of ⅛" extrudate alumina (Norton). After completion of the feeding of the ruthenium solution, the motor was rotated at the same speed for an additional 30 min. The ruthenium-supported alumina thus obtained was calcined at 550° C. for 6 hours under an air atmosphere in a muffle furnace. An X-ray fluorescence analysis showed that the content of ruthenium in the catalyst was 7.5 wt %.

EXAMPLES 1 TO 5

Continuous Preparation of Serinol

In a fully-automated, high pressure reactor (inner diameter 2.54 cm×length 60 cm) made of 316 stainless steel, 50 g of the (⅛)" extrudate type catalyst prepared in Preparation Example 2 was charged. After being purged with nitrogen, the reactor was heated from room temperature to 55° C. at a rate of 1° C. per min while hydrogen was fed into the reactor at 50 sccm. The amount of hydrogen was increased to the extent which was twice as much as that needed in the reaction. Separately, the nitropropanediol sodium salt prepared in Preparation Example 1 was dissolved in methanol and water to give a solution with a nitropropanediol sodium salt content of 5 wt %. This reactant solution was fed into the reactor. The feeding rate of the reactant and the reaction condition are shown in Table 1 below. Reaction products were taken every 4 hours for 20 hours in total and analyzed by gas chromatography (50 m×0.2 mm×0.5 μm PONA column) with a flame ionization detector (FID) and the results are given in Table 1 below.

TABLE 1

| No. of Examples | Temp. (° C.) | Press. (psig) | WHSV ($h^{-1}$) | Conversion (%) | Selectivity for Serinol (%) |
|---|---|---|---|---|---|
| 1 | 55 | 850 | 1.4 | 99.5 | 94.5 |
| 2 | 55 | 850 | 2.8 | 99.0 | 92.9 |
| 3 | 50 | 850 | 2.8 | 92.5 | 89.7 |
| 4 | 50 | 850 | 1.4 | 98.0 | 90.5 |
| 5 | 50 | 800 | 2.8 | 92.2 | 87.3 |

The conversion and the selectivity to serinol were determined with gas chromatographic analysis of trifluoroacetate, which was prepared by reacting serinol and trifluoroacetic anhydride (Plant Cell Physiol. 1986, 27(6), 1109).

EXAMPLES 6 TO 15

Continuous Preparation of Serinol

The hydrogenation of the nitropropanediol sodium salt prepared in Preparation Example 1 was carried out in a similar manner to that of Example 1 in a mixture solvent of 9:1 methanol:water under the condition of a temperature of 55° C., a hydrogen pressure of 870 psig and a WHSV of 1.4 $h^{-1}$ or 2.8 $h^{-1}$ in the presence of catalysts which were prepared in Preparation Example 2 or 3. The compositions of the catalysts, reaction conditions and results are given in Table 2, below.

TABLE 2

| No. of Examples | Catalysts | WHSV (h$^{-1}$) | Conversion (%) | Selectivity for Serinol (%) |
|---|---|---|---|---|
| 6 | 0.5% Pd/Al$_2$O$_3$ | 1.4 | 60.0 | 43.5 |
| 7 | 3% Ru/Al$_2$O$_3$ | 1.4 | 80.0 | 81.2 |
| 8 | 5% Ru/Al$_2$O$_3$ | 1.4 | 90.0 | 83.5 |
| 9 | 5% Ru/Al$_2$O$_3$ | 2.8 | 87.5 | 78.5 |
| 10 | 7.5% Ru/Al$_2$O$_3$ | 1.4 | 99.0 | 94.0 |
| 11 | 10% Ru/Al$_2$O$_3$ | 1.4 | 97.2 | 95.3 |
| 12 | 10% Ru/Al$_2$O$_3$ | 2.8 | 91.2 | 92.5 |
| 13 | 15% Pd/Al$_2$O$_3$ | 1.4 | 96.5 | 94.8 |
| 14 | 15% Pd/Al$_2$O$_3$ | 2.8 | 95.0 | 92.8 |
| 15 | 25% Pd/Al$_2$O$_3$ | 2.8 | 99.8 | 96.2 |

Comparative Examples 1 to 3

The hydrogenation of nitropropanediol sodium salt was carried out in a similar manner to that of Example 1 in a mixture solvent of methanol and water under the condition of a temperature of 55° C., a hydrogen pressure of 850 psig and a WHSV of 1.4 $^{-1}$ in the presence of catalysts shown in Table 3, below. These catalysts were not prepared according to the present invention, but commercially obtain from manufacturers. Their specifications were not given.

TABLE 3

| No. of C. Examples | Catalysts | Conversion (%) | Selectivity for Serinol (%) |
|---|---|---|---|
| 1 | 10% Pd/C | 91.0 | 87.5 |
| 2 | Degussa 5% Ru/Alumina | 91.9 | 83.0 |
| 3 | 5% Pd/Alumina | 90.5 | 82.5 |

EXAMPLE 16

Long-Term Continuous Reaction for Serinol

A long-term, continuous reaction was carried out in the presence of the catalyst prepared in Preparation Example 2 in a reactor similar to that of Example 1. The deactivation of the catalyst was not observed for 2,000 hours. The results are given in Table 4, below.

TABLE 4

|  | 500 hrs | 1,000 hrs | 1,500 hrs | 2,000 hrs |
|---|---|---|---|---|
| Conversion (%) | 98.5 | 98.4 | 98.4 | 98.0 |
| Selectivity (%) | 95.3 | 94.8 | 94.7 | 94.0 |

EXAMPLES 17 TO 21

Continuous Reaction and Separation of Serinol

Reaction was carried out in a reactor similar to that of Example 1 using 50 g of the catalyst prepared in Preparation Example 2. During the reaction, the pressure inside the reactor was maintained at 850 psig while the reaction temperature and WHSV were changed in the same manner as in Examples 1 to 5, After 200 hours of the reaction, the solution containing serinol was collected and was charged in a 10 liter glass reactor equipped with a vacuum distillator. The temperature of the glass reactor was elevated at a rate of 5° C. per min to 80° C. at which vacuum distillation was conducted under a pressure of 100 mbar to evaporate about 90% of methanol and water in the solution, and the sodium chloride filtered was removed. Then, 15 liter of isopropyl alcohol was added into the glass reactor and the temperature of the glass reactor was elevated at a rate of 5° C. per min to 80° C. at which vacuum distillation was conducted under a pressure of 100 mbar to remove isopropyl alcohol until the content of serinol reached 90 wt %. Next, vacuum distillation at 115 to 130° C. under 0.5 to 1 mbar afforded serinol powders. The purities and yields of the products are given in Table 5, below, along with reaction conditions.

TABLE 5

| No. of Examples | Temp. (° C.) | Press. (psig) | WHSV (h$^{-1}$) | Serinol Purity (%) | Serinol Yield (%) |
|---|---|---|---|---|---|
| 17 | 55 | 850 | 1.4 | 99.7 | 84.5 |
| 18 | 55 | 850 | 2.8 | 99.6 | 82.9 |
| 19 | 50 | 850 | 2.8 | 99.3 | 85.7 |
| 20 | 50 | 850 | 1.4 | 98.9 | 80.5 |
| 21 | 50 | 800 | 2.8 | 99.2 | 87.0 |

INDUSTRIAL APPLICABILITY

Consequently, the method of the present invention can produce serinol of a higher purity at a higher yield compared with conventional methods. Together with these advantages in purity and yield, its process simplicity brings about an economical favor in the serinol production and enables the method to be industrially applied for large scale production.

What is claimed is:

1. A method for preparing serinol through hydrogenation, comprising the steps of:

reacting 1 equivalent of nitromethane with 1 to 10 equivalents of para-formaldehyde and then, adding 0.5 to 5 equivalents of sodium hydroxide to give 2-nitro-1,3-propanediol sodium salt;

preparing a catalyst which comprises an inorganic support in which a catalytically effective metal component is impregnated at an amount of 1 to 20 wt %, said catalytically effective metal being selected from the group consisting of palladium (Pd), platinum (Pt), rhodium (Rh), iridium (Ir), ruthenium (Ru), osmium (Os) and mixtures thereof; and continuously hydrogenating the 2-nitro-1,3-propanediol sodium salt in an immobilized bed reactor in which the catalyst is packed.

2. The method as set forth in claim 1, wherein the reacting step for preparing the 2-nitro-1,3-propanediol sodium salt is carried out at a temperature of 0 to 100° C.

3. The method as set forth in claim 1, wherein the inorganic support is selected from the group consisting of alumina, silica, silica-alumina, zirconia, titania, zeolite and molecular sieves.

4. The method as set forth in claim 1, wherein the catalyst contains palladium or ruthenium at an amount of 5 to 20 wt %.

5. The method as set forth in claim 1, wherein the hydrogenating step is conducted at a temperature of 0 to 150° C. under a hydrogen pressure of 15 to 2,500 psig with a hydrogen flux at a weight hourly space velocity of 0.1 to 10 h$^{-1}$.

6. The method as set forth in claim 1, wherein the hydrogenating step is conducted with a molar ratio of hydrogen to 2-nitro-1,3-propanediol sodium salt ranging from 1 to 10.

7. The method as set forth in claim 1, wherein the hydrogenating step is conducted with a 1 to 50 wt % solution of 2-nitro-1,3-propanediol sodium salt in a solvent.

8. The method as set forth in claim 7, wherein the solvent is selected from the group consisting of methyl alcohol, ethyl alcohol, isopropyl alcohol, n-butyl alcohol, s-butyl alcohol, t-butyl alcohol, water and mixtures thereof.

9. The method as set forth in claim 8, wherein the solvent is a mixture of methyl alcohol and water.

10. The method as set forth in claim 8, wherein the solvent is a mixture of 9:1 methyl alcohol and water.

11. The method as set forth in claim 1, wherein the immobilized bed reactor is a trickle-bed reactor.

12. A method for preparing serinol through hydrogenation, comprising the steps of:

reacting 1 equivalent of nitromethane with 1 to 10 equivalents of para-formaldehyde and then, adding 0.5 to 5 equivalents of sodium hydroxide to give 2-nitro-1,3-propanediol sodium salt; and continuously hydrogenating the 2-nitro-1,3-propanediol sodium salt in the presence of the metal catalyst selected from the group consisting of palladium (Pd), platinum (Pt), rhodium (Rh), iridium (Ir), ruthenium (Ru), osmium (Os) and mixtures thereof in an immobilized bed reactor in which the catalyst is packed.

\* \* \* \* \*